(12) United States Patent
Naffa'a et al.

(10) Patent No.: US 10,447,199 B2
(45) Date of Patent: Oct. 15, 2019

(54) AUTOMATED SOLAR PANEL CLEANING

(71) Applicant: Saudi Arabian Oil Company, Dhahran (SA)

(72) Inventors: Ahmad Mamoun Naffa'a, Dhahran (SA); Saeed Aljabri, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 0 days.

(21) Appl. No.: 15/838,068

(22) Filed: Dec. 11, 2017

(65) Prior Publication Data

US 2019/0181799 A1   Jun. 13, 2019

(51) Int. Cl.
| | | |
|---|---|---|
| *B08B 3/04* | (2006.01) | |
| *H02S 40/10* | (2014.01) | |
| *H02S 50/00* | (2014.01) | |
| *B08B 3/02* | (2006.01) | |
| *G01N 21/17* | (2006.01) | |

(Continued)

(52) U.S. Cl.
CPC ............... *H02S 40/10* (2014.12); *B08B 3/02* (2013.01); *B08B 3/04* (2013.01); *E03B 3/28* (2013.01); *G01N 21/17* (2013.01); *G05B 19/0428* (2013.01); *H02S 50/00* (2013.01); *B08B 2203/0223* (2013.01); *G05B 2219/24015* (2013.01)

(58) Field of Classification Search
CPC . H02S 40/10; H02S 50/00; B08B 3/02; B08B 2/04; B08B 2202/0223; E03B 3/28; G01N 21/17; G05B 19/0428; G05B 2219/24015
See application file for complete search history.

(56) References Cited

U.S. PATENT DOCUMENTS 6,182,453 B1   2/2001   Forsberg
9,475,707 B2   10/2016  John et al.
(Continued)

FOREIGN PATENT DOCUMENTS

| GB | 1548205 A | 7/1979 |
| WO | 2013/030844 A1 | 3/2013 |
| WO | 2016/114814 A1 | 7/2016 |

OTHER PUBLICATIONS

Mohammed Atta, "Solar Water condensation using thermoelectric coolers", International Journal of Water Resources and Arid Environments 1(2); 142-145-2011 (Year: 2011).*

*Primary Examiner* — Sharidan Carrillo
(74) *Attorney, Agent, or Firm* — Leason Ellis LLP

(57) ABSTRACT

A method for automatically cleaning a solar panel using an atmospheric water generator is provided. The method includes the steps of generating water using the atmospheric water generator. The water can be stored for using in a cleaning operation. The system can monitor the efficiency of the solar panel power generation. If the efficiency drops below a certain level, which can indicate that the solar panels are dirty, the system can automatically initiate a cleaning operation. The stored water can be pumped through pipes and nozzles to clean the solar panels. The system can automatically initiate the atmospheric water generator to replenish the used water. The system can use a portion of the power generated by the solar panels to perform the cleaning and water generation operations. Accordingly, an automatic and self-contained solar panel cleaning method and system is provided.

5 Claims, 2 Drawing Sheets

(51) Int. Cl.
  *G05B 19/042* (2006.01)
  *E03B 3/28* (2006.01)

(56) References Cited

U.S. PATENT DOCUMENTS

| | | |
|---|---|---|
| 2010/0043851 A1* | 2/2010 | Levy ........................ B08B 3/02 |
| | | 134/56 R |
| 2012/0138123 A1 | 6/2012 | Newdoll et al. |
| 2014/0100698 A1* | 4/2014 | Suresh .................... H02S 40/10 |
| | | 700/275 |
| 2015/0136196 A1 | 5/2015 | Williamson |
| 2015/0251225 A1 | 9/2015 | Jagannathan |
| 2016/0056755 A1* | 2/2016 | Abiko ...................... H02S 40/10 |
| | | 136/246 |
| 2017/0104451 A1 | 4/2017 | Gostein |
| 2018/0287552 A1* | 10/2018 | Tomlinson .............. F24S 40/20 |

\* cited by examiner

US 10,447,199 B2

AUTOMATED SOLAR PANEL CLEANING

FIELD OF THE INVENTION

The present invention provides for automated solar panel cleaning and, in particular, automated solar panel cleaning using atmospheric water generation.

BACKGROUND OF THE INVENTION

Solar panels are used to generate electricity by absorbing sunlight as a source of energy. Solar panels mainly include, photovoltaic (PV) modules that provide the photovoltaic arrays of a solar PV system. A solar PV system typically includes an array of PV modules, an inverter, a battery or number of batteries for electrical storage and wiring connections. Solar panels are used in a wide range of industrial and residential applications to provide electrical power from solar energy, and in many applications solar panels exist in completely remote areas. The efficiency of solar panels decreases and is affected by dust and stains on the panels, therefore panels require cleaning, particularly in remote areas that are often subject to extreme environments that promote soiling of the solar panels (e.g., deserts).

Since solar panels at remote areas are difficult to clean due to a number of issues, including: (a) acceptability in the locale which may lead to increase of safety risks; (b) availability of a cleaning fluid source (e.g., water); and (c) availability of personnel to clean the panels.

As such, a method of cleaning solar panels has become needed to overcome the above-mentioned difficulties. A major difficulty is the availability of water to clean the panels, especially at remote areas. As a result, if water is made available at remote areas close to solar panels, and the cleaning process of panels can be performed without interference of personnel in a systematic and automated way, the issue of cleaning solar panels can be resolved. The present invention such a system that solves these and other problems as disclosed herein.

DETAILED DESCRIPTION CERTAIN OF EMBODIMENTS OF THE INVENTION

Figure 1:
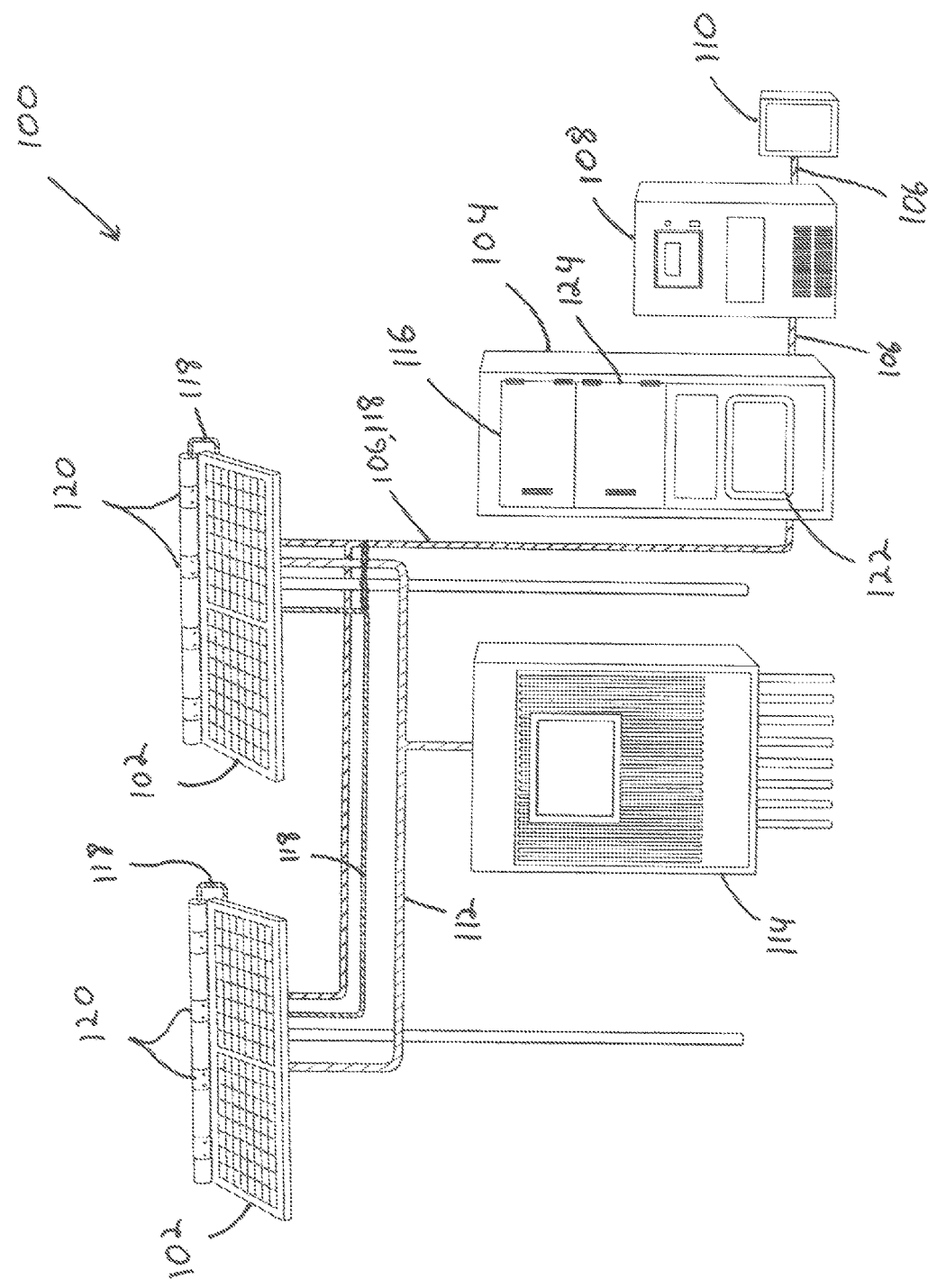
FIG. 1 shows a schematic illustration of the system in accordance with one embodiment of the present invention.

Referring to FIG. 1, an embodiment is illustrated of an automatic solar cleaning (ASC) system 100. The ASC system 100 includes a plurality of solar panels 102. The solar panels 102 can be part of a solar power generation system (e.g., solar farm). The solar panels 102 can be part of a large-scale power generation system in which hundreds of solar panels are grouped together (e.g., in a plurality of rows) in an area. However, the ASC system 100 can also be used in connection with smaller scale systems (e.g., roof top application and on commercial and residential properties).

Several factors are taken into account for placement of solar panels, including hours and intensity of solar radiation and availability of land. Accordingly, solar panels may be located in remote and/or arid, dessert regions. However, as part of regular solar panel maintenance, solar panels require periodic cleaning. Due to the remote and/or arid regions in which the solar panels can be located, sources of water (e.g., ground water, surface water, rain water, municipal water) may be unavailable. As such, an atmospheric water generator (AWG) 104 is provided to collect moisture directly from the humidity in the atmosphere. The water generated can be collected and stored and then used for cleaning solar panels, as discussed in more detail below.

The AWG 104 operates based on the refrigeration cycle and uses condensation coils to cause ambient humidity found in air to condense on the coils and form water droplets. One example of an AWG is disclosed in U.S. Pat. No. 6,182,453 to Forsberg, which is incorporated by reference herein in its entirety. As more water condenses the droplets are collected and stored in a reservoir tank. The AWG 104 can be scaled up or down in size in order to meet the water generation requirement for solar panel cleaning operations. For example, a large scale solar farm can be equipped with a large AWG unit that includes several, large condenser coils to generate larger amounts of water and/or several AWG units can be employed at various locations to service the solar farm.

The AWG 104 requires a power source to run its various electronics and condenser pumps. Accordingly, the AWG 104 can be connected to one or more of the solar panels 102 of solar array via, for example, electrical wires 106. As the AWG 104 requires power to operate, the power can be drawn directly from the solar panels 102. A solar power inverter 108 can be provided to convert the energy collected by the solar panels into electricity that can be used to power the AWG 104 directly and/or charge a battery 110. For example, the solar inverter 108 converts the variable direct current (DC) output of a photovoltaic solar panel into an alternating current (AC), which can be used by the AWG. The AWG 104 can also include its own dedicated solar panel(s) for power generation so that tying into the power generations systems of the array of solar panels 102 is not required. A battery 110 can provided to deliver power to the AWG 104. For example, power generated by the solar panels 102 occurs during the day when the sun is shining. However, this may not be the best time to operate the AWG 104 as environmental air humidity can be higher during overcast days and/or during the night. As such, it can be more efficient to operate the AWG 104 to generate water during these times when the solar panels 102 are not generating electricity. The battery 110 can store electricity from the solar panels 102 during peak solar power generation conditions and the charged battery 110 can then be used at a different time (e.g., at night) by the AWG 104 during favorable atmospheric water generation conditions.

Power that is generated by the solar panels 102 that is not used for the automatic water generator 104 or for cleaning operations is, for example, sent to the regional power grid as part of normal power generation operations. Load electrical wires 112 are provided to send power to the load power handler unit 114, which sends the power generated by the solar panels to the power grid.

After the AWG 104 has generated water, the water can be stored in a storage tank 116 that can be internal to the AWG 104 and/or can include an external storage tank. The AWG 104 can operate to generate water until a sufficient level of water is collected in the storage tank 116 in order to supply water to perform a cleaning operation.

A system of pipes 118 are connected to the AWG 104 and storage tank 116 so that the collected water can be directed onto the solar panels 102 for cleaning. An array of spray nozzles 120 can be provided for each solar panel unit. Since solar panels are typically tilted at an angle in order to more efficient catch sunlight, the spray nozzles 120 can be placed at an upper side of the solar panels 102. As such, as water is sprayed onto the surface of the solar panels 102 from the nozzles 120, gravity causes the water to move across the surface of the solar panels and drip off the lower side. The spraying of the water and/or the movement of the water across the surface of the solar panels 102 acts to remove debris (e.g., dust and/or other deposits) from the surface of the solar panels 102. The system can include a pump 122 (e.g., internal or external to the AWG 104) that can increase the pressure of the water being delivered through the pipes 118 and nozzles 120. Indeed, for many installations in which the solar panel arrays are placed at a higher elevation than the AWG 104, the pump 122 is essential to elevate the water up the pipe connections to the spraying nozzle 120, as shown in FIG. 1. While it can be desirable to include pump 122 to provide water pressure for the cleaning operations in any arrangement, in certain arrangements it is possible to position the AWG 104 and/or storage tank (e.g., vertically above the plane of the solar panels) so that the water can be gravity feed through the pipes. In certain arrangements, a lower side collection system can be used to collect the water that drips off the solar panels after cleaning. The collected water can then be cleaned to remove the collected debris from the water and the water can be recycled to use for future cleaning operations. The recycling of this water can reduce the load on the AWG's need to generate all the water required for the system.

The AWG 104 can also include a drinking water access port 124. Since the water generated by the AWG 104 is collected directly from the atmosphere, it is naturally of high quality and low in contaminants. Accordingly, the water can be used for drinking by personnel working on the solar panel site, which is especially useful in emergency situations given the potential remoteness of the site.

Figure 2:
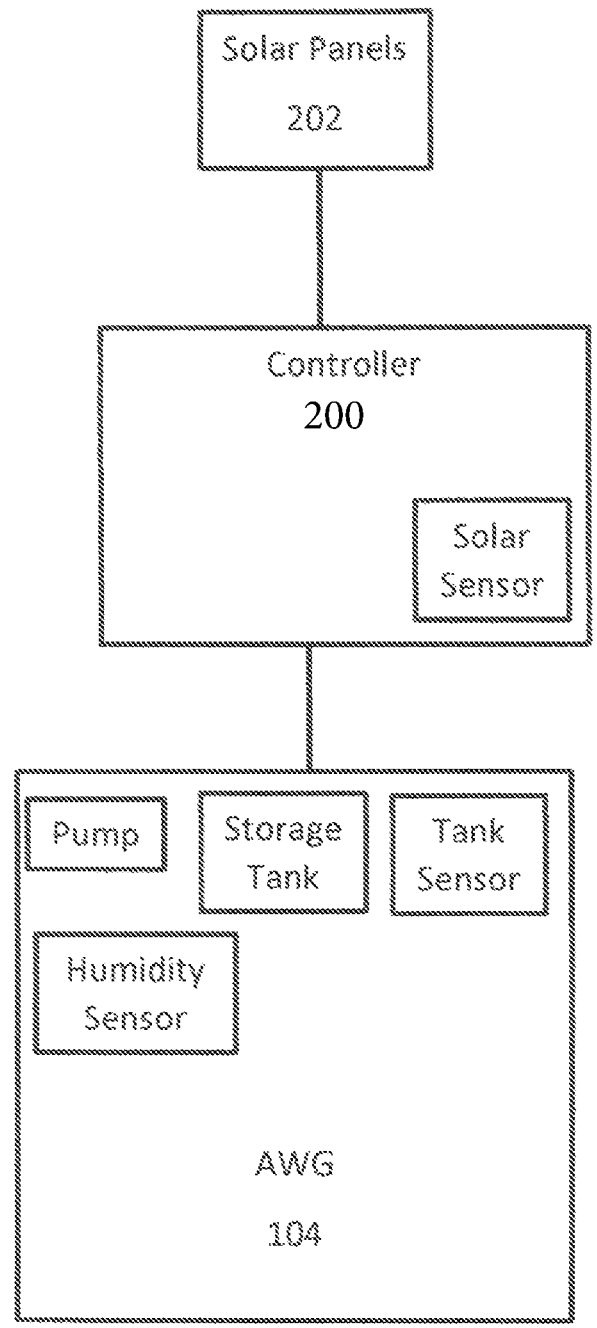
FIG. 2 shows a block diagram in accordance therewith.

Referring to FIG. 2, a controller 200 can control the operation of the various systems of the ASC system 100. The controller is configured by code which is implemented or executed within a processor associated with the controller. Memory of conventional design is employed by the controller, as is other conventional hardware to enable the controller to respond to conditions (signals) and implement commands based on its programming. The controller 200 can provide a signal to provide power to operate the pump 122 that provides to the solar panels for cleaning. For example, solar panels can be cleaned on a regular time interval such as every 30 minutes, 60 minutes, 120 minutes or other time intervals. These intervals can be stored in the memory and referenced by the code implemented in or executed by the processor of the controller. The controller 200 can also monitor the output of the solar panels 102 via signals from sensors associated with the panels in order to determine whether the solar panels 102 are generating energy (e.g., when the sun is out during the day time and/or the sun is not obscured by clouds) and to limit the cleaning operations to only times when the solar panels 102 are generating energy (e.g., cleaning can only occur when power generation levels are over a certain threshold) so that water and power associated with the cleaning operation is not wasted by cleaning panels that are not generating power. The controller performs such monitoring and cleaning-cycle limiting by comparing values associated with the sensed signals to stored threshold values and making determinations as to whether to initiate or suppress or delay a cleaning cycle in accordance with its programming. The system (i.e., the controller 200) can also include a solar sensor that measures solar output in order to determine whether there is sufficient solar power generation potential (e.g., over a threshold level) to warrant performing a cleaning operation, as determined by code implemented in or executing in the processor of the controller.

Moreover, the system can perform spot cleaning by only operating a portion of the solar panels (e.g., by operating a smaller, separate pump and pipe system) to clean, for example, a single solar panel and/or the solar sensor. The controller, again using code implemented or executed therein, can compare the power output and/or solar radiation levels before (e.g., as may be stored in the memory for later reference) and after the spot cleaning (again, using data stored in the memory) to determine the power generation efficiency reduction due to dirt (as opposed to other factors such as clouds). If the programming of the controller is such that the comparison results in a determination that there has been an improvement after cleaning above a threshold amount (i.e, the improvement has been mathematically significant), the controller can send a signal, based on its programming, to the pump to pump water to clean the remainder of the solar panels. The system can use an efficiency threshold such that if the power generation efficiency drops below a certain level, the controller can initiate a cleaning cycle. As one example, the controller can compare the amount of energy being lost due to a reduced efficiency of the solar panel power generation to the amount of energy required to perform a cleaning operation, again, using programming executing or implemented in its processor. If the loss in generated energy (e.g., due to dirty panels) outweighs the power consumption to perform a cleaning operation, the controller can initiate a cleaning cycle.

The controller 200 can also control the operation of the AWG system 104. For example, a humidity sensor can measure the atmospheric humidity to determine whether or not there are efficient conditions for water generation operation. In general, the higher the atmospheric humidity, the more efficiently the AWG system 104 can generate water. If the humidity is above a threshold, programming in the controller 200 can cause a signal to be sent to the AWG system 104 to begin generating water. In certain conditions, the threshold for operation of the AWG system 104 can automatically be changed by the controller 200 depending on various factors accounted for in the controller's programming, including, for example, the power generation efficiency of the solar panels 102. For example, if the solar panels 102 are very dirty there is a higher value to cleaning the solar panels. Accordingly, the threshold for AWG operation can be lowered so that water can be generated to clean the solar panels even if the atmospheric humidity is relatively low. On the other hand, if the solar panels are generating power at a high efficiency (e.g., they are relatively clean) there is less of a need for water generation for cleaning so the AWG threshold can be raised. Similarly, the AWG operation threshold can be adjusted based on stored water levels. If water levels are high (e.g., there is a relatively large reserve of water) the AWG threshold can be raised so that water generation only occurs in efficient, favorable conditions and when water levels are low (e.g., there is a greater need to replenish water) the threshold can be lowered so that water is generated even when conditions are less than optimal.

In addition, when water is abundant (e.g., storage levels are high) and AWG conditions are favorable (e.g., high atmospheric humidity) the controller can initiate cleaning operations more frequently to keep the solar panels generating electricity at peak performance since the costs of generating water is relatively low.

The controller 200 can automatically initiate a cleaning operation and can automatically initiate the AWG to generate water, and the system can further operate using power generated by the solar panels, with programming executing in the processor to configure the controller in that way. Accordingly, the system can operate in a self-contained, automated manner to generate power while also maintaining the solar panels with periodic cleaning. The controller 200 can use various sensor data, such as stored water levels, solar power generation efficiency, solar radiation levels, and atmospheric humidity levels, among others, to control operation of the cleaning system (e.g., running of the pump) and the AWG system to generate water. Moreover, the system can use weather data (current, past, and/or predicative) to control operation of the system. For example, if it has recently rained, it is currently raining, or it is predicted to rain in the near future, the controller can delay a cleaning operation since the rain may obviate the need to perform a water spray cleaning in view of the fact that the rain water failing on the solar panels may act to clean the panels.

As one example of operation, the controller 200 measures the current solar power generation output by the solar panels. The current solar generation output is compared to a reference level of solar generation output (e.g., after to solar panels have been recently cleaned), using programming implemented in or executed by the processor of the controller. If the difference is above a certain threshold amount (referenced from memory), which can indicate that the solar panel are dirty, the controller can next determine the level of stored water via a reading of signals from a water level sensor. If the water level is above a threshold sufficient to perform a cleaning operation, the controller can send a signal to operate the pump, which pumps water through the pipes and nozzles to clean the solar panels. If the water is not sufficient to perform a cleaning operation, the controller can send a signal to the AWG to start generating water. Again, this is all a function of the programming in the controller, which is understood to respond to comparisons of stored data, sensed data, interpolated or extrapolated data, using code which references such data in a conventional way to perform the novel function of this particular application. Once a sufficient amount of water has been generated, the controller can end the AWG water generation operation and initiate the pump to begin a cleaning operation. The duration of the cleaning operation can be a time interval, for example, after which the controller can stop the cleaning operation. The operation of the AWG can also be based on anticipated water needs for cleaning such that the controller can initiate the AWG to generate water in advance of a cleaning operation so that cleaning can be performed on demand.

The subject matter described above is provided by way of illustration only and should not be construed as limiting. Various modifications and changes can be made to the subject matter described herein without following the example embodiments and applications illustrated and described, and without departing from the true spirit and scope of the present invention, which is set forth in the following claims.

Notably, the figures and examples above are not meant to limit the scope of the present application to a single implementation, as other implementations are possible by way of interchange of some or all of the described or illustrated elements. Moreover, where certain elements of the present application can be partially or fully implemented using known components, only those portions of such known components that are necessary for an understanding of the present application are described, and detailed descriptions of other portions of such known components are omitted so as not to obscure the application. In the present specification, an implementation showing a singular component should not necessarily be limited to other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present application encompasses present and future known equivalents to the known components referred to herein by way of illustration.

The foregoing description of the specific implementations will so fully reveal the general nature of the application that others can, by applying knowledge within the skill of the relevant art(s) (including the contents of the documents cited and incorporated by reference herein), readily modify and/or adapt for various applications such specific implementations, without undue experimentation, without departing from the general concept of the present application. Such adaptations and modifications are therefore intended to be within the meaning and range of equivalents of the disclosed implementations, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s). It is to be understood that dimensions discussed or shown are drawings are shown accordingly to one example and other dimensions can be used without departing from the invention.

While various implementations of the present application have been described above, it should be understood that they have been presented by way of example, and not limitation. It would be apparent to one skilled in the relevant art(s) that various changes in form and detail could be made therein without departing from the spirit and scope of the application. Thus, the present application should not be limited by any of the above-described example implementations.

The invention claimed is:

1. A method for automatically cleaning a solar panel using an atmospheric water generator, comprising the steps of:
measuring an amount of stored water;
measuring an atmospheric humidity level;
obtaining weather data;
automatically adjusting at least one of a water threshold and a humidity threshold in view of the measured amount of stored water, the measured atmospheric humidity level, and the weather data;
comparing the measured amount of stored water to the adjusted water threshold;
comparing the measured atmospheric humidity level to the adjusted humidity threshold;
generating water using the atmospheric water generator upon a determination that the measured amount of stored water is above the adjusted water threshold and the humidity level is above the adjusted humidity threshold;
storing the water generated by the atmospheric water generator;
monitoring an efficiency of power generated by the solar panel to determine a reduction in solar power generation efficiency;
comparing the reduction of solar power generation efficiency to a solar power generation threshold;

initiating a cleaning operation upon a determination that the reduction of solar power generation efficiency is above the solar power generation threshold; and delivering the stored water through a system of pipes and nozzles to spray the water onto the surface of the solar panels to clean the solar panels.

2. The method of claim 1, wherein the step of generating water using the atmospheric water generator further includes the steps of:

comparing the reduction of solar power generation efficiency to an atmospheric water generation operation power consumption; and operating the atmospheric water generator to generate water upon a determination that reduction of solar power generation efficiency outweighs the water generation operation power consumption.

3. The method of claim 1, wherein the step of generating water using the atmospheric water generator occurs in advance of a cleaning operation.

4. The method of claim 1, further including the steps of:

measuring a solar radiation level; and comparing the solar radiation level to a solar radiation threshold;

wherein the cleaning operation is initiated upon a determination that the solar radiation level is above the solar radiation threshold.

5. A method for automatically cleaning a solar panel system using an atmospheric water generator, comprising the steps of:

generating water using the atmospheric water generator;

storing the water generated by the atmospheric water generator;

measuring a first power generated by a solar panel system;

spot cleaning a portion of the solar panel system;

measuring a second power generated by the solar panel system after the spot cleaning;

comparing the first power generated to the second power generated to determine a reduction in power generation efficiency;

comparing the reduction of power generation efficiency to a solar power generation threshold;

initiating a cleaning operation of the solar panel system upon a determination that the reduction of solar power generation efficiency is above the solar power generation threshold; and pumping the stored water through a system of pipes and nozzles to spray the water onto the surface of the solar panel system to clean the solar panel system.

* * * * *